(12) United States Patent
Shiba et al.

(10) Patent No.: US 9,815,866 B2
(45) Date of Patent: Nov. 14, 2017

(54) PEPTIDES THAT BIND TO EPITHELIAL CELL ADHESION MOLECULE

(71) Applicant: JAPANESE FOUNDATION FOR CANCER RESEARCH, Tokyo (JP)

(72) Inventors: Kiyotaka Shiba, Tokyo (JP); Katsutoshi Kokubun, Tokyo (JP); Kanako Suga, Tokyo (JP)

(73) Assignee: JAPANESE FOUNDATION FOR CANCER RESEARCH, Tokyo (JP)

( * ) Notice: Subject to any disclaimer, the term of this patent is extended or adjusted under 35 U.S.C. 154(b) by 242 days.

(21) Appl. No.: 14/428,017

(22) PCT Filed: Sep. 12, 2013

(86) PCT No.: PCT/JP2013/074655
§ 371 (c)(1),
(2) Date: Mar. 13, 2015

(87) PCT Pub. No.: WO2014/042209
PCT Pub. Date: Mar. 20, 2014

(65) Prior Publication Data
US 2015/0246945 A1    Sep. 3, 2015

(30) Foreign Application Priority Data
Sep. 14, 2012    (JP) .................... 2012-203464

(51) Int. Cl.
| | | |
|---|---|---|
| C07K 7/06 | (2006.01) | |
| C07K 7/08 | (2006.01) | |
| G01N 33/574 | (2006.01) | |
| C07K 14/705 | (2006.01) | |
| C07K 14/47 | (2006.01) | |
| C07K 16/00 | (2006.01) | |
| G01N 33/68 | (2006.01) | |

(52) U.S. Cl.
CPC ............. *C07K 7/06* (2013.01); *C07K 7/08* (2013.01); *C07K 14/47* (2013.01); *C07K 14/70596* (2013.01); *C07K 16/005* (2013.01); *G01N 33/574* (2013.01); *G01N 33/6872* (2013.01); *C07K 2319/00* (2013.01); *C07K 2319/60* (2013.01); *G01N 2333/70596* (2013.01)

(58) Field of Classification Search
CPC combination set(s) only.
See application file for complete search history.

(56) References Cited

U.S. PATENT DOCUMENTS

| | | | | |
|---|---|---|---|---|
| 2008/0229451 | A1* | 9/2008 | Cao ............ | C07K 14/195 800/281 |
| 2009/0324575 | A1* | 12/2009 | Shayman ............ | C12Q 1/44 424/94.6 |

FOREIGN PATENT DOCUMENTS

| | | | |
|---|---|---|---|
| EP | 2402754 | A2 * | 1/2012 |
| EP | 2402754 | A2 * | 2/2012 |
| JP | 3916653 | | 2/2007 |
| JP | 2008-533587 | | 8/2008 |
| JP | 4592752 | | 9/2010 |
| JP | 2011-193728 | | 10/2011 |
| JP | 4843505 | | 10/2011 |
| WO | 2006/064639 | | 6/2006 |
| WO | 2006/068250 | | 6/2006 |
| WO | 2006/096139 | | 9/2006 |
| WO | 2006/126595 | | 11/2006 |

OTHER PUBLICATIONS

Japanese Foundation for Cancer Research, Bunshi Imaging Kiki Kenkyu Kaihatsu Project/Shinki kusei Shuyo Bunshi Probe no Kiban Gijutsu Kaihatsu/Bunshi Probe Yoso Gijutsu no Kaihatsu Akusei Shuyo Tokuiteki Jinko Peptite Aptamer no 'Sono Ba' Soshutsu Oyobi Nano Zairyo o Mochiita Bunshi Probe-ka Gijutsu no Kaihatsu, New Energy and Industrial Technology Development Organization (NEDO) Heisei 20 to 21 Nendo Seika Hokokusho, May 3, 2011 (May 3, 2011), pp. 1 to 21, Listed in International Search Report, brief English description.

Iwasaki K., et al., Carcinomas Cell Imaging by Using EpCAM-binding Peptides Selected from the Cyclic Non-standard Peptide Library., Peptide science 2010: Proceedings of the Fifth International Peptide Symposium, Mar. 2011, p. 114, Listed in International Search Report, English text.

Seigneuric R., et al., From Nanotechnology to Nanomedicine: Applications to Cancer Research., Current Molecular Medicine, 2010, vol. 10, pp. 640-652, English text.

Colorectal carcinoma-specific antigen: Detection by means of monoclonal antibodies, Meenhard Herlyn et al., pp. 1438-1442, discussed in specification, English text.

Transcription factors and molecular epigenetic marks underlying EpCAM overexpression in ovarian cancer, van der Gun BT., et al., pp. 312-319, discussed in specification, English text.

(Continued)

*Primary Examiner* — Lei Yao
(74) *Attorney, Agent, or Firm* — Rankin, Hill & Clark LLP

(57) ABSTRACT

[Problem to be Solved]
An object of the present invention is to provide a novel peptide that has the high ability to bind to EpCAM, which can be easily prepared by a chemical synthesis method or a genetic engineering method.

[Solution]
The present inventors have improved a method for screening a phage library and thereby successfully screened for a peptide that has the higher ability to bind to EpCAM compared with publicly known peptides. The present inventors have also used an already disclosed peptide having the ability to bind to EpCAM as a lead compound to prepare diverse populations of derivatives thereof, from among which a peptide strongly binding to EpCAM has been selected. The obtained peptides exhibit at least 10 times higher ability to bind to EpCAM compared with publicly known peptides and as such, are effective for the detection or diagnosis of cancer cells.

13 Claims, 13 Drawing Sheets

(56) References Cited

OTHER PUBLICATIONS

EpCAM an immunotherapeutic target for gastrointestinal malignancy: current experience and future challenges, MA Chaudry et al., pp. 1013-1019, discussed in specification, English text.
Catumaxomab, Clinical development and future directions, Rolf Linke et al., pp. 129-136, discussed in specification, English text.
Molecular Cancer Research, A Complex of EpCAM, Claudin-7, CD44 Variant Isoforms, and Tetraspanins Promotes Colorectal Cancer Progression, Sebastian Kuhn et al., pp. 553-567, discussed in specification, English text.
Fabrication of Nickel and Chromium Nanoparticles Using the Protein Cage of Apoferritin, Mitsuhiro Okuda et al., pp. 187-194, discussed in specification, English text.
International Search Report, dated Dec. 3, 2013 (Dec. 3, 2013).

* cited by examiner

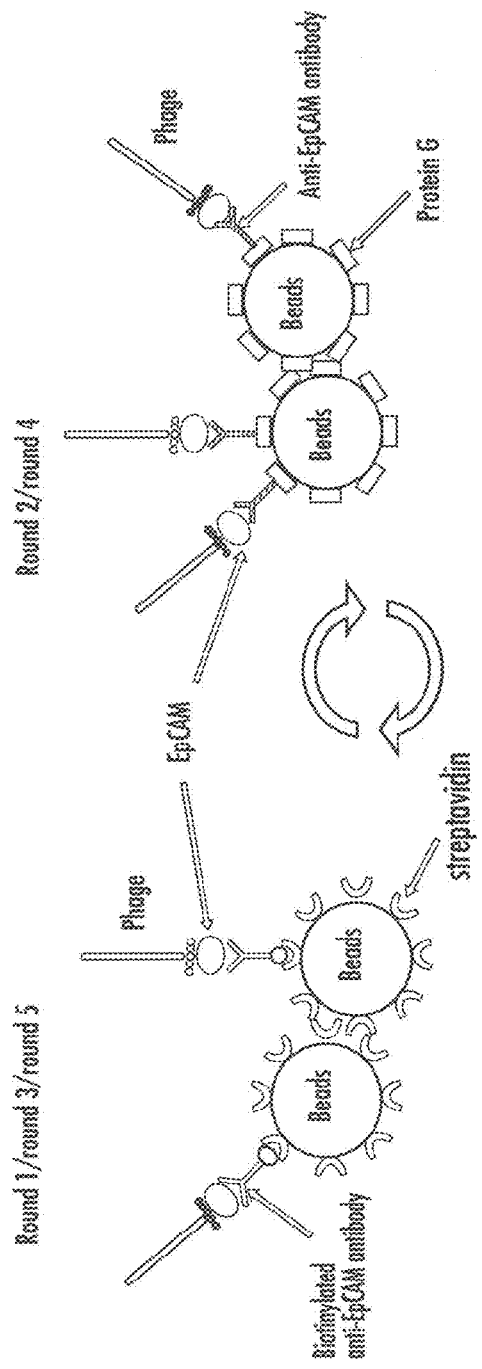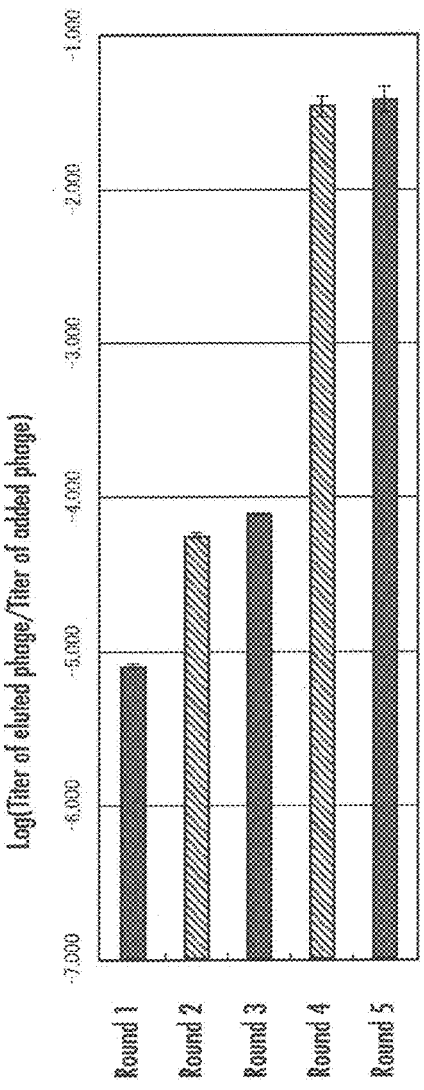

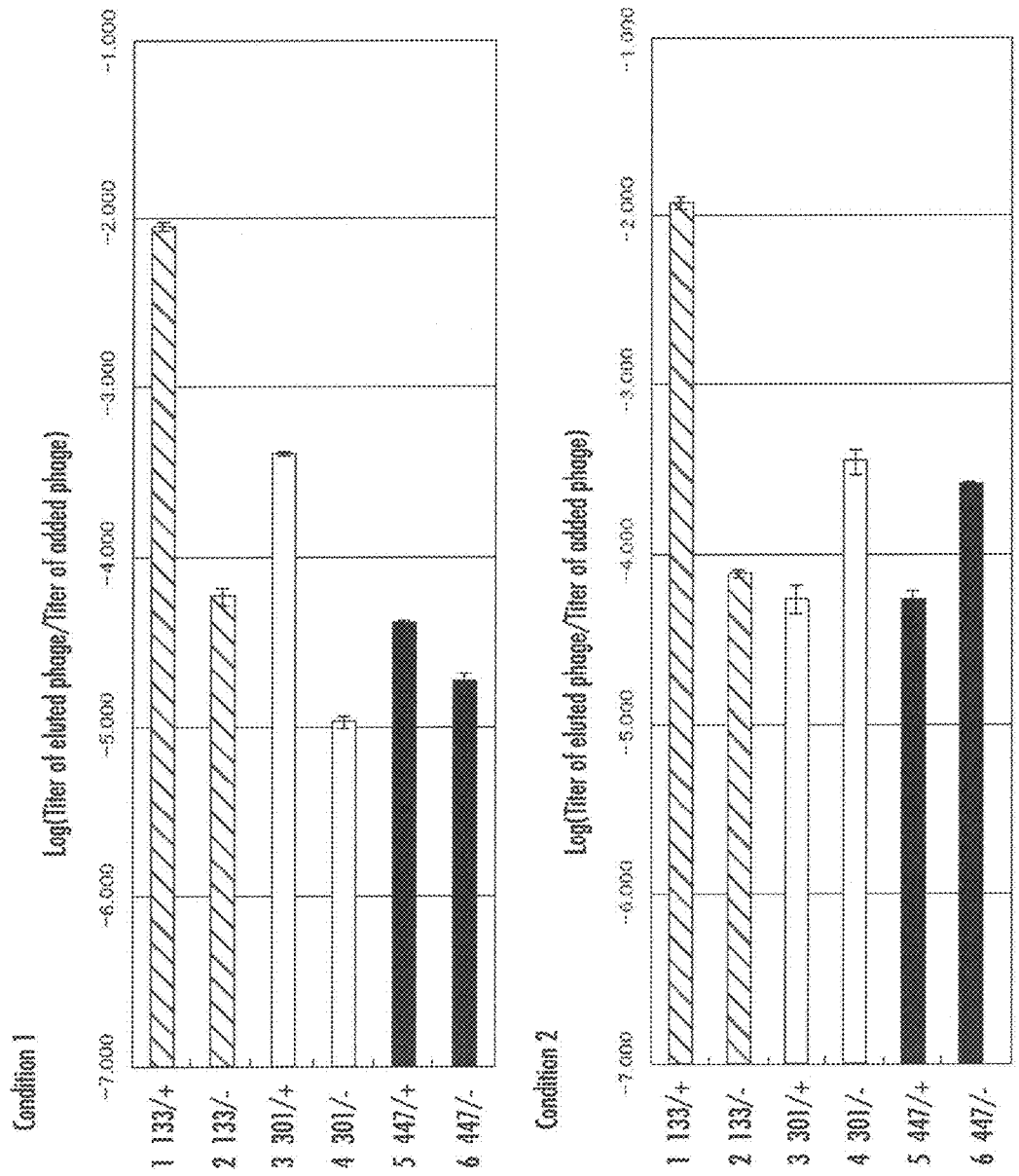

FIG.5A
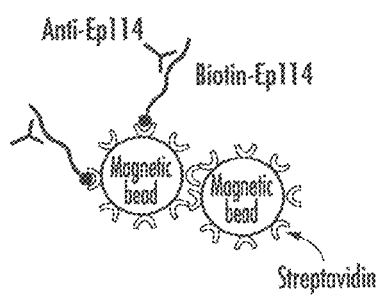
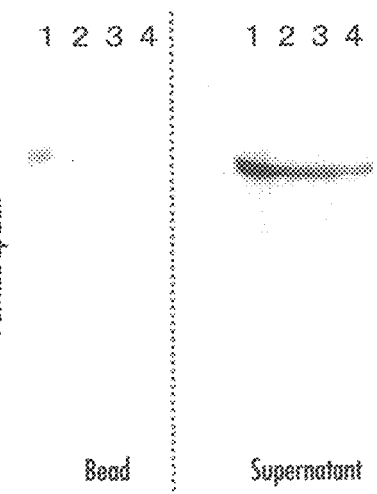
FIG.5B
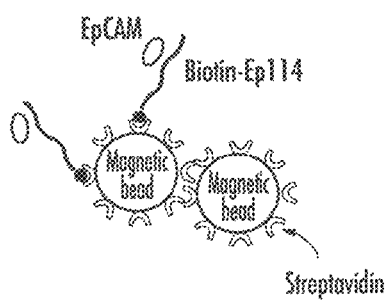
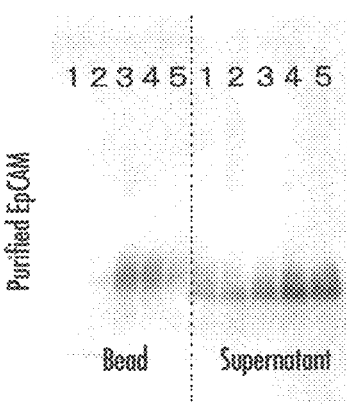
FIG.5C
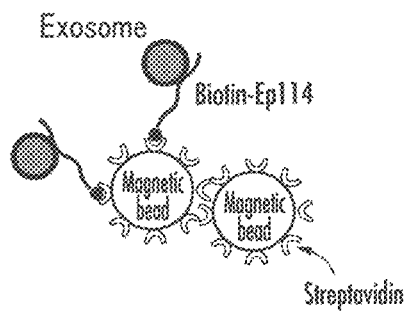
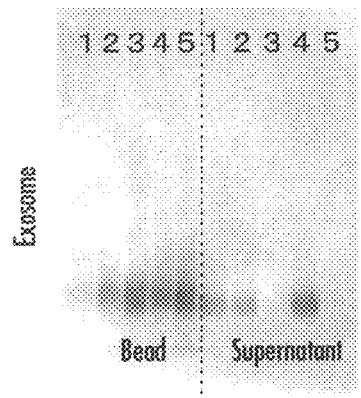

FIG. 6
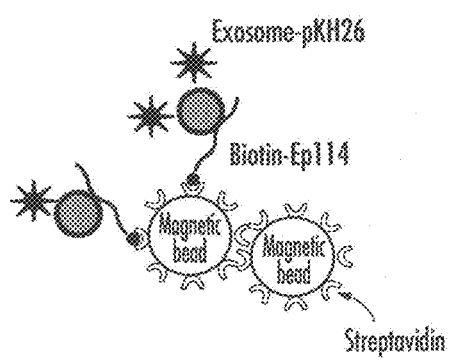
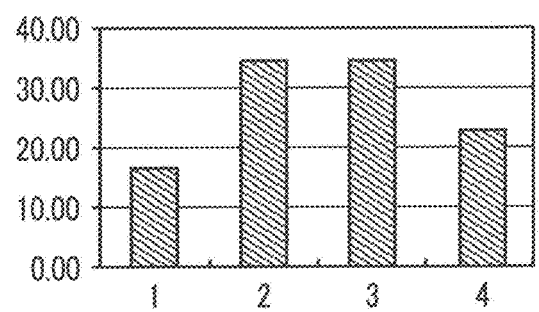

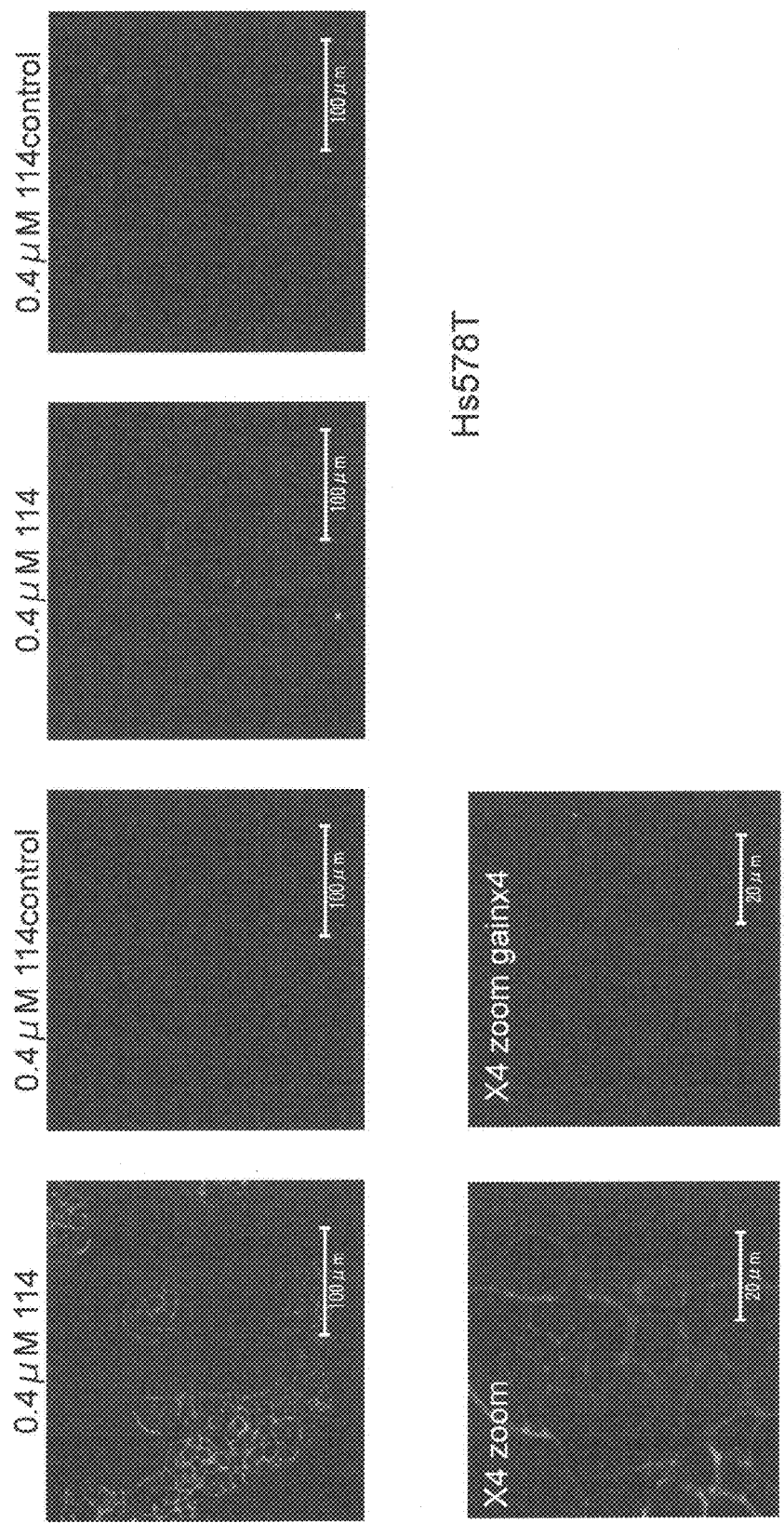

PEPTIDES THAT BIND TO EPITHELIAL CELL ADHESION MOLECULE

TECHNICAL FIELD

The present invention relates to a peptide that has the high ability to bind to EpCAM, a derivative of the peptide such as a fusion protein comprising the peptide, an antibody recognizing the peptide, a method using the peptide for detecting or quantifying EpCAM, and a composition comprising the peptide for diagnosing cancer.

BACKGROUND ART

Epithelial cell adhesion molecule (EpCAM; CD326) is a type I membrane protein that has been reported as a cancer-specific cell surface antigen expressed in colorectal cancer (Non Patent Literature 1). EpCAM is expressed mainly on the basal membranes of epithelial cells in normal tissues. However, because its expression is observed in most of cancer cells of epithelial origin, EpCAM has been known as a so-called cancer antigen and has been shown to be useful as a diagnostic marker (Non Patent Literature 2).

As the sensitive techniques to detect cancer cells have been established in recent years, it has been found that tumor cells exist and circulate in blood: circulating tumor cells. The presence of the circulating tumor cells is closely associated with metastasis of cancer and is therefore very important for prognostic prediction. Since EpCAM is detected in most of cancer cells of epithelial origin, as mentioned above, prognostic prediction by a method which involves collecting cells having the EpCAM antigen on their surface with an antibody and detecting this antibody has already been practiced (Patent Literature 1).

It has also been shown that EpCAM dissociate from the surface of tumor cells to increase significantly its concentration in the serum of malignant tumor patients, suggesting that EpCAM can be used not only as a surface marker of tumor cells but as a tumor marker in serum.

Furthermore, in addition to its diagnostic benefit, the therapeutic benefit of EpCAM has been shown in recent years. Cancer vaccines have already been developed by use of EpCAM, and vaccine therapies have also been reported, in which EpCAM proteins prepared with an insect cell expression system such as a baculovirus system, or anti-idiotype antibodies binding to the antigen recognition site of an anti-EpCAM antibody are used. In addition, anti-EpCAM antibodies for cancer treatment have also been developed, and clinical trials are underway using anti-EpCAM antibodies such as Adecatumumab (MT201) and ING-1. The treatment using these antibodies is intended to reduce the size of tumor by cellular immunity (cytotoxic activity) induced by binding of the antibody to EpCAM on the surface of tumor cells through the patient's own immune system. For the purpose of enhancing the cytotoxic activity of the anti-EpCAM antibodies, Proxiniums Vivendiums (VB4-845) which is an anti-EpCAM antibody fused with a *pseudomonas* exotoxin, EMD 273 066 (huKS-IL2) which is an anti-EpCAM antibody fused with IL-2, EU-approved Catumaximab which also has anti-CD3 activity, and the like have been further developed (Non Patent Literatures 3 and 4).

As mentioned above, EpCAM is very important for the diagnosis, prognostic prediction, and treatment of cancer, and the efficacy of molecules specifically binding to EpCAM, such as antibodies, in the diagnosis and treatment of cancer have been established. In addition to the antibodies mentioned above, α-actinin, claudin 7, CD44v4-v7 (a splicing valiant of CD44), D6.1A protein (a kind of tetraspanin), and the like are known as the molecules that bind to EpCAM specifically (Non Patent Literature 5).

CITATION LIST

Patent Literature

Patent Literature 1: National Publication of International Patent Application No. 2008-533587
Patent Literature 2: Japanese Patent Laid-Open No. 2011-193728
Patent Literature 3: Japanese Patent No. 4843505
Patent Literature 4: Japanese Patent No. 3916653
Patent Literature 5: Japanese Patent No. 4592752

Non Patent Literature

Non Patent Literature 1: Herlyn M et al., Proc Natl Acad Sci USA, 1979, Vol. 76: p. 1438-1442,
Non Patent Literature 2: van der Gun B T., Br J Cancer. 2011, Vol. 105 (2), p. 312-319
Non Patent Literature 3: Chaudry M A., Br J Cancer. 2007, Vol. 96 (7), p. 1013-1019
Non Patent Literature 4: Linke R, MAbs. 2010, Vol. 2 (2), p. 129-136
Non Patent Literature 5: Kuhn, S. et al., Mol Cancer Res., 2007, Vol. 5, p. 553-567
Non Patent Literature 6: Okuda, M. et al., Biotechnol Bioeng. 2003, Vol. 84, p. 187-194

SUMMARY OF INVENTION

Technical Problem

Unfortunately, previously known antibodies or molecules having the ability to bind to endogenous EpCAM require high cost because their isolation or preparation is laborious work. In the case of antibodies prepared using a cell culture system, the possibility of contamination by toxic substances during protein preparation cannot be ruled out and extreme safety measures should be taken when these antibodies are used in treatment.

Accordingly, as a post-antibody drug or a post-antibody diagnostic agent, there has been a demand for a compound having the ability to bind to EpCAM, which can be prepared inexpensively without the use of a cell culture system.

To overcome the problems mentioned above, the present inventors have already disclosed a peptide having the ability to bind to EpCAM, which can be prepared easily using a chemical synthesis method or a genetic engineering technique (Patent Literature 2). This peptide was identified by contacting a population of phages displaying diverse peptide sequences on phage particles with an immobilized EpCAM protein, and recovering the phage particles bound to the EpCAM protein, followed by selection of the phage clones that specifically bind to EpCAM. The analysis of the DNA sequence of this phage clone revealed that the peptide specifically binding to EpCAM had the amino acid sequence of KSLQCINNLCWP (SEQ ID NO: 5). This peptide was designated as Ep301.

However, the ability of the peptide Ep301 to bind to EpCAM was weak. Although the peptide exhibits the ability to bind thereto on the phage, the ability to bind to EpCAM is weakened by separation from the phage. The peptide therefore presents a problem associated with accuracy for use in diagnosis or the like and is also difficult to use in treatment.

Thus, an object of the present invention is to provide a peptide that has the strong ability to bind to EpCAM and thereby effectively recognizes EpCAM-expressing cells, and to provide various methods for detecting EpCAM using the peptide.

Solution to Problem

To solve the problem, the present inventors have improved a method for screening a phage library and thereby successfully cloned a clone Ep133 that has the strong ability to bind to EpCAM.

The present inventors have also used Ep301 as a lead compound to prepare a diverse population of derivatives thereof, and have cloned Ep114 from this library successfully, which bind more strongly to the EpCAM molecule.

Specifically, the present invention relates to a peptide having the ability to bind to EpCAM, the peptide comprising an amino acid sequence shown in SEQ ID NO: 1 (XHLXCXXXXCWX).

From sequence analysis on these obtained two peptides that strongly bind to EpCAM, it is considered that the 2nd, 3rd, 5th, 10th, and 11th amino acids in their sequences are conserved as histidine, leucine, cysteine, cysteine, and tryptophan, respectively, and these amino acids in the sequences are very important for strong binding to EpCAM.

Since a peptide comprising a sequence in which these 5 amino acids are conserved is likely to strongly bind to EpCAM, a library containing such sequences with the conserved amino acids can be prepared and screened to thereby further obtain a novel peptide having the high ability to bind to EpCAM.

The present invention also relates to a peptide that has the sequence of SEQ ID NO: 2 (EHLHCLGSLCWP; Ep133) or SEQ ID NO: 3 (KHLQCVRNICWS; Ep114).

These two peptides bind approximately 10 times more strongly compared with the peptide Ep301 already disclosed by the present inventors. Thus, EpCAM can be detected with a high sensitivity, and highly accurate diagnosis can therefore be achieved.

The present invention further relates to any of the peptides labeled with a detectable marker, a fusion peptide comprised of any of the peptides and a marker protein and/or a peptide tag, an EpCAM-peptide complex in which any of the peptides or the fusion peptide is bound with EpCAM, a phage characterized by displaying any of the peptides on the surface of the particle thereof and having the ability to bind to EpCAM, an antibody recognizing any of the peptides.

Binding of a detectable marker, a tag, or the like to the peptide mentioned above enables various applications and the peptides can therefore be widely exploited in diagnosis. Also, EpCAM can be sensitively detected by use of the peptide in a form displayed on a phage or an antibody recognizing the EpCAM-binding peptide. As a result, the accuracy of diagnosis can be enhanced.

The present invention further relates to a DNA encoding any of the peptides, a recombinant vector (particularly, a recombinant plasmid vector) which comprises the DNA and is capable to express a peptide that has the ability to bind to EpCAM, and a transformant harboring the recombinant vector.

Use of the DNA or the recombinant vector encoding any of the peptides enables the EpCAM-binding peptide to be produced conveniently in large amounts by use of publicly known genetic engineering techniques.

The present invention further relates to a method for detecting or quantifying EpCAM using any of the peptides or the fusion peptide. Because the peptides disclosed in the present invention have the high ability to bind to EpCAM, EpCAM can be detected very sensitively and thereby quantified reliably using the peptides.

Since the expression of EpCAM is found in most cancers that have epitherial origin, highly accurate reliable detection enables diagnosis of cancer using the EpCAM peptide. Particularly, since EpCAM is known to an associated with metastasis of cancer, the prognosis of cancer can be accurately predicted.

BRIEF DESCRIPTION OF DRAWINGS

FIG. 1A showing the schematic diagram of a biopanning method for EpCAM using a D-12 phage library, FIGS. 1B and 1C showing the result of the biopanning, and the graph the ability of phages to bind to EpCAM under different immobilization conditions.

FIG. 5A-5C showing an example of the application of EpCAM detection for an immunoprecipitation method using Ep114, and the role of a linker.

FIG. 6 showing a detection method using fluorescently labeled exosomes.

FIG. 10 showing staining of cells with an EpCAM peptide.

DESCRIPTION OF EMBODIMENTS

Figure 2A:
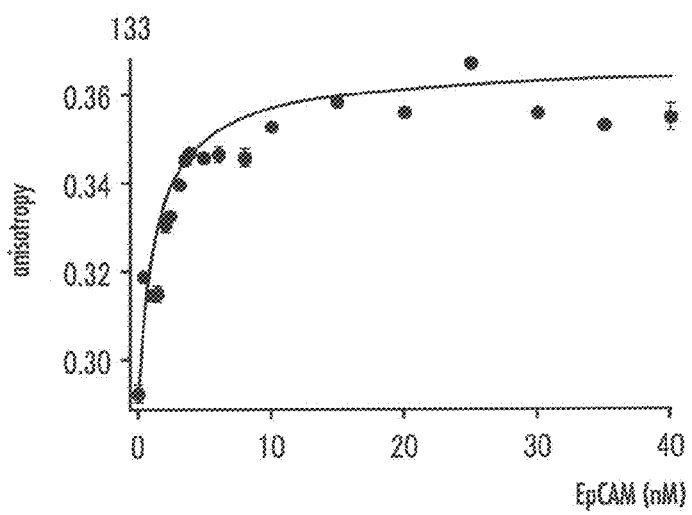
FIG. 2A-2F showing results of the binding of EpCAM-binding peptides to EpCAM measured by a fluorescence depolarization method.
Figure 2B:
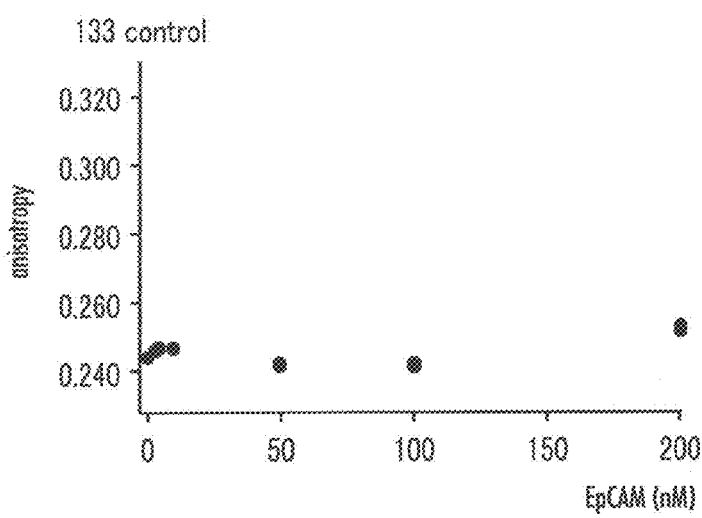

After extensive studies, the present inventors successfully cloned two types of peptides (disclosed as SEQ ID NOs: 2 and 3) that strongly bind to EpCAM.

The amino acid sequence EHLHCLGSLCWP shown in SEQ ID NO: 2 (hereinafter, this peptide is referred to as Ep133) and the amino acid sequence KHLQCVRNICWS shown in SEQ ID NO: 3 (hereinafter, this peptide is referred to as Ep114) have the ability to bind to EpCAM at least 10 times higher compared with the EpCAM-binding peptide Ep301 (sequence: KSLQCINNLCWP, SEQ ID NO: 5) which is previously developed by the present inventors.

Peptides that have the common amino acid sequence XHLXCXXXXCWX (SEQ ID NO: 1) conserved in these two types of peptides of SEQ ID NOs: 2 and 3 may include a peptide that strongly binds to EpCAM. Thus, with use of a peptide library comprising the above sequence, it can be expected to clone a novel peptide having the high ability to bind to EpCAM.

Each peptide of the present invention mentioned above can be produced by a general chemical synthesis method according to its amino acid sequence.

The above peptide of the present invention can also be prepared by a routine method using genetic engineering techniques on the basis of the nucleotide sequence information DNA encoding the peptide of the present invention that has the ability to bind to EpCAM. The thus-obtained peptide of the present invention that has the ability to bind to EpCAM can be appropriately purified according to a general method, for example, a method generally used in the field of peptide chemistry, such as ion-exchange resins, partition chromatography, gel chromatography, affinity chromatography, high-performance liquid chromatography (HPLC), or a countercurrent distribution method.

The peptide of the present invention may be labeled with a detectable marker, which is not particularly limited as long as the marker is a conventionally known marker for labeling peptides. Specific examples thereof can include: radioisotopes such as $^3$H, $^{14}$C, and $^{125}$I; fluorescent materials such as dansyl chloride and tetramethylrhodamine isothiocyanate; organism-derived molecules generally used as biochemical research tools, such as biotin and digoxigenin; bioluminescent compounds; chemiluminescent compounds; metal chelates; and image processing agents.

The peptide of the present invention may be a fusion peptide of the peptide and a marker protein and/or a peptide tag. The fusion peptide of the present invention can be any fusion protein as long as the peptide of the present invention having the ability to bind to EpCAM is bound with a marker protein and/or a peptide tag. The marker protein or the peptide tag is not particularly limited as long as the marker protein or the peptide tag is conventionally known. Specific examples of the above marker protein can include: enzymes such as alkaline phosphatase and horseradish peroxidase (HRP); Fc regions of antibody; fluorescent proteins such as GFP; GST; maltose-binding protein (MBP); and ferritin. Specific examples of the peptide tag can include: epitope tags such as HA, FLAG, and Myc; and affinity tags such as biotinylated peptides and oligohistidine. Such a labeled peptide or a fusion peptide of the present invention can be prepared by a published method and is useful not only in the purification of the peptide of the present invention or the detection of the peptide of the present invention but in the detection or quantification of EpCAM in a test sample, and in the detection or separation of cells expressing EpCAM.

The present invention further encompasses an EpCAM-peptide complex in which the peptide or the fusion peptide is bound with the EpCAM protein. The EpCAM-peptide complex of the present invention is not particularly limited as long as the complex in which the peptide or the fusion peptide of the present invention is bound with EpCAM, and can be usefully used in the functional analysis of EpCAM at the molecular level such as a study on the interaction of EpCAM with other intracellular molecules.

The phage of the present invention that has the ability to bind to EpCAM can be any phage as long as the phage displays, on the surface of its particle, the peptide of the present invention that has the ability to bind to EpCAM. The phage that has the ability to bind to EpCAM can be obtained by separating a peptide-presenting phage that binds strongly to EpCAM from other phage populations in the course of screening a phage library having the amino acid sequence of SEQ ID NO: 1, and can also be obtained by incorporating a DNA encoding the peptide of the present invention that has the ability to bind to EpCAM into a phagemid vector using a routine method and transforming host cells such as *E. coli* with the vectors and then infecting the host cells with helper phages.

Specific examples of antibodies recognizing the peptide of the present invention can include monoclonal antibodies, polyclonal antibodies, chimeric antibodies, single-chain antibodies, and humanized antibodies. These antibodies can be prepared by a routine method using the peptide of the present invention as an antigen.

The antibodies against the peptide of the present invention are produced by immunizing an animal with the peptide of the present invention or a fragment thereof using a protocol commonly used. Specifically, the peptide of the present invention is synthesized and bound to a carrier protein such as keyhole limpet hemocyanin, and used to immunize an animal such as a rabbit, a goat, or a mouse. After confirmation of a rise in antibody titer, the serum is collected.

Any of methods can be used in the preparation of the monoclonal antibodies including a hybridoma method (Nature, 1975, Vol. 256, p. 495-497), a trioma method, a human B cell hybridoma method (Immunology Today, 1983, Vol. 4, p. 72), and an EBV-hybridoma method (Monoclonal Antibodies and Cancer Therapy, 1985, pp. 77-96, Alan R. Liss, Inc.), in which antibodies are prepared from cultures of continuous cell-culture systems.

The recombinant vector of the present invention is not particularly limited as long as the recombinant vector comprises the DNA of the present invention and is capable to express a peptide that has the ability to bind to EpCAM. The recombinant vector of the present invention can be constructed by properly inserting the DNA of the present invention into an expression vector, preferably, an expression plasmid vector. The expression vector is preferably a vector capable of replicating autonomously in host cells or a vector capable of being integrated into the chromosomes of host cells. Also, a vector containing control sequences such as a promoter, an enhancer, and a terminator at positions that enable transcription of the DNA of the present invention can be preferably used.

Examples of the expression vector include pCMV6-XL3 (Origin Technologies Corp.), EGFP-C1 (Clontech Laboratories, Inc.), pGBT-9 (Clontech Laboratories, Inc.), pcDNAI (Funakoshi Corp.), pcDM8 (Funakoshi Corp.), pAGE107 (Cytotechnology, 1990, Vol. 3, p. 133), pCDM8 (Nature, 1987, Vol. 329, p. 840), pcDNAI/AmP (Invitrogen Corp.), pREP4 (Invitrogen Corp.), pAGE103 (J. Biochem., 1987, Vol. 101, p. 1307), and pAGE210. Examples of the promoter can include the human cytomegalovirus (CMV) IE (immediate early) gene promoter, the SV40 early promoter, a retroviral promoter, the metallothionein gene promoter, the heat shock gene promoter, and SRα promoter. A reporter gene such as a gene encoding a fluorescent protein can be further fused downstream of the promoter. Examples of the fluorescent protein can include green fluorescent protein (GFP), cyan fluorescent protein (CFP), blue fluorescent protein (BFP), yellow fluorescent protein (YFP), red fluorescent protein (RFP), and luciferase.

The EpCAM-binding peptide of the present invention may be fused with ferritin, a part of ferritin, or modified ferritin by methods disclosed in Patent Literatures 3 to 5, and the resulting fusion product can be used to prepare a nanocarrier having the ability to bind to the EpCAM protein wherein the nanocarrier comprises an inorganic material such as iron, magnetite, gold, or a compound semiconductor. The fusion with a magnetic inorganic material such as iron or magnetite enables separation by magnetic force, and the fusion with magnetite enables the resulting product to be used in MRI.

The transformant of the present invention is not particularly limited as long as the transformant results from the transfer of the recombinant vector of the present invention to a host cell and expresses the peptide of the present invention having the ability to bind to EpCAM. Examples thereof can include transformed yeasts, transformed plants (cells, tissues, and individuals), transformed bacteria, and transformed animals (cells, tissues, and individuals), and preferably transformed animal cells.

The peptide or the fusion peptide of the present invention can be used in the detection or quantification of EpCAM. The method for detecting or quantifying EpCAM according to the present invention can be any method using the peptide or the fusion peptide of the present invention. In the case of using the peptide of the present invention labeled with a detectable marker or the fusion peptide of the present invention, a appropriate detection or quantification method can be selected according to the type of the labeling material such as the marker used. The method for detecting or quantifying EpCAM may use the peptide of the present invention and the antibody of the present invention in combination. For example, after the peptide of the present invention is bound to EpCAM, the peptide can be recognized by the antibody of the present invention, and then detected with a labeled second antibody, and this enables detection with a high sensitivity. Furthermore, the label on the secondary antibody recognizing the antibody of the present invention can be changed to thereby enable convenient application to a known immunological assay method such as RIA, ELISA, immunostaining, or Western blot.

The peptide or the fusion peptide of the present invention can be further used to detect or separate EpCAM-expressing cells. The peptide of the present invention labeled with a detectable marker or the fusion peptide of the present invention can be used for the detection of the EpCAM-expressing cells. Also, the EpCAM-expressing cells can be separated by a publicly known separation method according to the type of the labeling material such as the marker used. When a fluorescent material, for example, is used as the labeling material, the EpCAM-expressing cells can be separated efficiently and highly accurately by flow cytometry with fluorescence as an index.

The composition for diagnosing cancer of the present invention is not particularly limited as long as the composition comprises the peptide of the present invention or the fusion peptide of the present invention. The composition for diagnosing cancer of the present invention can also be used in combination with the antibody of the present invention.

Hereinafter, the present invention will be described with reference to Examples. However, the technical scope of the present invention is not intended to be limited by these Examples.

Example 1

[Screening for Ep133]

1. Phage Library

Ph.D.-12 peptide phage display kit (New England Biolabs Inc.) was used in this screening. This library was a phage library displaying 12-residue linear random peptides and has diversity of $2.7 \times 10^9$.

2 Panning

A method for panning is schematically shown in FIG. 1(A). In order to remove phages adsorbed nonspecifically, phages were first allowed to bind to beads on which only antibodies were immobilized but purified EpCAM were not, and then phages that did not bind to the beads were recovered and used. This operation was carried out before every round to remove nonspecifically adsorbed phages. Biotinylated polyclonal EpCAM antibodies were immobilized on Dynabeads® M-280 coated with streptavidin, and these beads are used for the immobilization of EpCAM. The panning was carried out in TBST (0.01% Tween 20 and Tris buffered saline). 3 µg of EpCAM was immobilized on the beads. The phages were added to the EpCAM-immobilized beads. After washing, phages eluted from the beads by acid treatment were allowed to grow in E. coli, and subjected to the 2nd round of screening.

A plasmid containing EpCAM cDNA was constructed in pINCY (Open Biosystems, Inc., MHS-1010-74356) with insertions myc and His tags at the C terminus of the extracellular domain, and was used to express the EpCAM protein in HEK-293T cells for purification.

In the 2nd round of biopanning, 2.4 µg of monoclonal EpCAM antibody (Vu-1D9, Abcam plc.) was immobilized on Dynabeads® PROTEIN G coated with 300 µg of Protein G, and 3 µg of the purified EpCAM was further bound to the beads. The phages obtained in the 1st round were added thereto at a titer of $1 \times 10^{11}$. After washing, phages eluted from the beads by acid treatment were allowed to grow in E. coli, and subjected to the 3rd round of palming. Subsequently, the 3rd and 5th rounds of palming were carried out under the same conditions as in the 1st round of panning, and the 4th round of panning was carried out under the same conditions as in the 2nd round of panning.

The ratio of the titer of the finally eluted phages to the titer of the phages added to the EpCAM-immobilized beads was determined and plotted by the round (FIG. 1B).

The titer ratio was compared among the 1st, 3rd, and 5th rounds and between the 2nd and 4th rounds of panning, which were carried out under the same conditions. In either case, the ratio of the titer of the eluted phages to the titer of the added phages was increased after each round, indicating that the enrichment of the phages that bind to EpCAM progressed.

Measurement of titer and amplification of phages were carried out according to routine methods (Phage Display-A Laboratory Manual, Cold Spring Harbor Laboratory Press, 2001). For the phage amplification, an ER2738 strain [F'lacI$^q$Δ (lacZ)M15 proA$^+$B$^+$zzf:Tn10(TetR) fhuA2 supE thi Δ(lac-proAB) Δ(hsdMS-mcrB)5 (rk$^-$mk$^-$McrBC$^-$)] in logarithmic growth phase was used.

3. Sequencing of phage clones

Eleven phages eluted in the 4th round of panning were randomly selected, and the sequences of peptides displayed by these phages were determined by a routine method according to the DNA sequence of relevant part (Phage Display A Laboratory Manual, Cold Spring Harbor Laboratory Press, 2001).

The nucleotide sequences were determined by the dideoxy termination method using a primer (−96gIII sequencing primer: SEQ ID NO: 4 (ccctcatagt tagcgtaacg)) corresponding to a complementary chain of a nucleotide sequence located 96 bases downstream from the displayed peptide region (CEQ DTCS Quick start kit, Beckman Coulter Inc.). A capillary sequencer was used for the electrophoresis and data analysis of the reaction products. As a result, all of the 11 clones displayed a peptide having the identical sequence which was termed as Ep133. The sequence of Ep133 was EHLHCLGSLCWP (SEQ ID NO: 2).

The cloned phage displaying Ep133 was used to analyze the ability of the phage to bind to EpCAM under different immobilization conditions (FIG. 1C). The binding ability of the Ep133-displaying phage was compared with that of the EpCAM-binding peptide Ep301 which was already disclosed by the present inventors in Patent Literature 2 and with that of a phage displaying no peptide (#447). The conditions used are as follows.

Under Condition 1, each phage (in FIG. 1C, rows 1 and 2 represent the Ep133-displaying phage, rows 3 and 4 represent the Ep301-displaying phage, and rows 5 and 6 represent the phage 447 displaying no peptide) was added at a titer of $1 \times 10^{10}$ to 0.4 mg of TALON® beads immobilized 1 µg of EpCAM (FIG. 1C, rows 1, 3, and 5, indicating with plus sign) or the beads alone (FIG. 1C, rows 2, 4, and 6, indicating with minus sign). After washing with TBST five times, the titers of bound phages were measured.

Under Condition 2, 2.4 µg of anti-EpCAM monoclonal antibody (Vu-1D9, Abcam plc.) was immobilized on Protein G beads, and 3 µg of purified EpCAM was immobilized thereon via the antibody. Each phage (in FIG. 1C, rows 1 and 2 represent the Ep133-displaying phage, rows 3 and 4 represent the Ep301-displaying phage, and rows 5 and 6 represent the phage 447 displaying no peptide) was added at a titer of $1 \times 10^{10}$ to the beads immobilized EpCAM (FIG. 1C, rows 1, 3, and 5, indicating plus sign) or the beads alone (FIG. 1C, rows 2, 4, and 6, indicating with minus sign). After washing with TBST once, the titers of bound phages were measured.

As shown in FIG. 1C, under both of the conditions, the Ep133-displaying phage exhibited at least approximately 10 times higher ability to bind to EpCAM compared with Ep301 on the condition that the immobilized beads were used.

Example 2

[Screening for Ep114]
1. Phage library

A library ((KR)-X-(LIMV)-Q-C-(ILMV)-X-(NQHK)-(ILMV)-C-W-X) (SEQ ID NO: 6) was constructed and used for screening, in which four amino acids at positions 4, 5, 10, and 11 were conserved and other moieties were diversified because the alanine scanning analysis of the sequence (KSLQCINNLCWP, SEQ ID NO: 5) of the EpCAM-binding peptide Ep301 previously disclosed in Patent Literature 2 showed the importance of these four residues for binding to EpCAM. This library has diversity of $9.8 \times 10^7$.

2 Panning 1.5 µg of biotinylated polyclonal EpCAM antibodies was immobilized on 300 µg of Dynabeads® M-280 coated with streptavidin, and 100 ng of purified EpCAM was added thereto to immobilize EpCAM onto the beads. The panning was carried out in TBST. In order to remove phages adsorbed nonspecifically, phages were first allowed to bind to beads on which only antibodies were immobilized and purified EpCAM were not, and phages that did not bind to the beads were recovered and used. The phages were added at a titer of $1 \times 10^{11}$ to the EpCAM-immobilized beads and adsorbed thereon for 15 minutes in with the presence of 100 µM Ep133 as a competitor. The adsorbed phages were recovered by acid treatment, and allowed to grow in E. coli, and used in the next round of panning. The 2nd and later rounds were carried out under the same conditions as above to perform a total of 5 rounds of panning.

Measurement of titer and amplification of phages were carried out according to routine methods (Phage Display-A Laboratory Manual, Cold Spring Harbor Laboratory Press, 2001). For the amplification of phages, an ER2738 strain [F' lacI$^q$Δ (lacZ)M15 proA$^+$B$^+$zzf::Tn10(TetR) thuA2 supE thi Δ(lac-proAB) Δ(hsdMS-mcrB)5 (rk$^-$ mk$^-$ McrBC$^-$)] in logarithmic growth phase was used.

3. Sequencing of Phage Clone

The sequence was determined in the similar way as in Example 1. An EpCAM-binding peptide screened for as a peptide having the high ability to bind to EpCAM, Ep114, had a sequence of KHLQCVRNICWS (SEQ ID NO: 3).

4. Conserved Residues in EpCAM-Binding Peptides

Based on the sequences of the peptides Ep133 and Ep114 which were obtained in Examples 1 and 2 and strongly bound to EpCAM, the 2nd, 3rd, 5th, 10th, and 11th amino acids in their sequences are conserved and important for the high ability to bind to EpCAM. Therefore, a peptide having the amino acid sequence XHLXCXXXXCWX of SEQ ID NO: 1 is expected to have the high ability to bind to EpCAM.

Thus, screening of a peptide library in which these 5 amino acid residues are conserved may lead to select a new peptide having the high ability to bind to EpCAM.

Example 3

[Measurement of Dissociation Constant of a EpCAM-Binding Peptide and EpCAM by Fluorescence Depolarization Method]

The obtained EpCAM peptides were assayed for their strength of binding to EpCAM by the fluorescence depolarization method, which is a method for evaluating the interaction between molecules. Each fluorescently labeled EpCAM peptide and EpCAM are used to determine the strength of binding from the kinetics of depolarization by Brownian movement.

Each FITC-modified EpCAM peptide or control peptide was suspended at a concentration of approximately 100 µM in PBS. After centrifugation, the supernatant was collected and diluted 10-fold, and the absorbance was measured at 495 nm From the measurement value, the molar concentration of the peptide was determined using the formula of Beer-Lambert of the following expression 1:

$$A = E \times b \times C \quad \text{[Expression 1]}$$

(A: absorbance, E: molar absorption coefficient (L/mol·cm), b: optical path length (cm), C: molar concentration)

EpCAM is diluted with PBS into several concentrations from 0 until reaching equilibrium (40 nM for the Ep133 peptide), and the FITC-modified peptide whose precise concentration has been measured by the aforementioned method is added to the dilutions thus prepared. The sample was left at a temperature for measurement for 30 minutes or longer and subjected to polarization measurement using a spectrofluorometer FP-6500 (JASCO Corp.) equipped with an automatic polarization measurement unit (JASCO Corp., APH-103). The obtained measurement results are shown in FIG. 2 and Table 1. Kd was estimated by curve fitting according to the Hill equation.

Figure 2C:
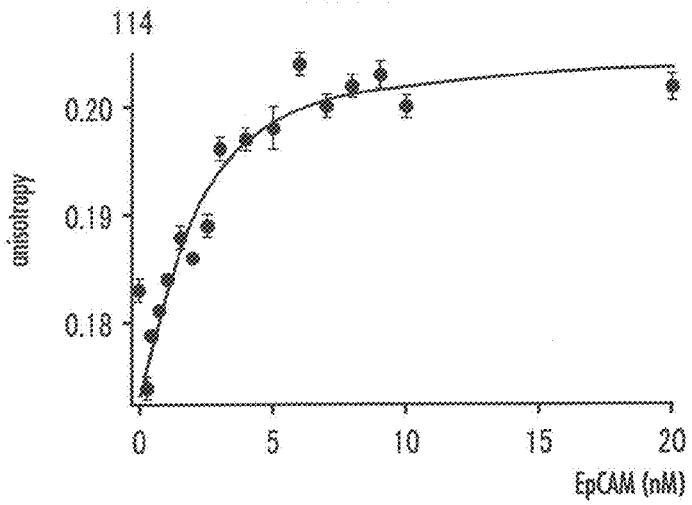

The dissociation constants of the two types of peptides Ep133 (FIG. 2(A)) and Ep114 (FIG. 2(C)), which were obtained in the present invention and had the high ability to bind to EpCAM, were measured by the fluorescence depolarization method. Since the analysis of the present inventors revealed that both the EpCAM-binding peptides have two conservative cysteine residues and require the formation of an S—S bond for their binding to EpCAM, Ep133 control (FIG. 2(B)), which had the substitution of cysteine at positions 5 and 10 by serine in Ep133, was used as a control.

Figure 2D:
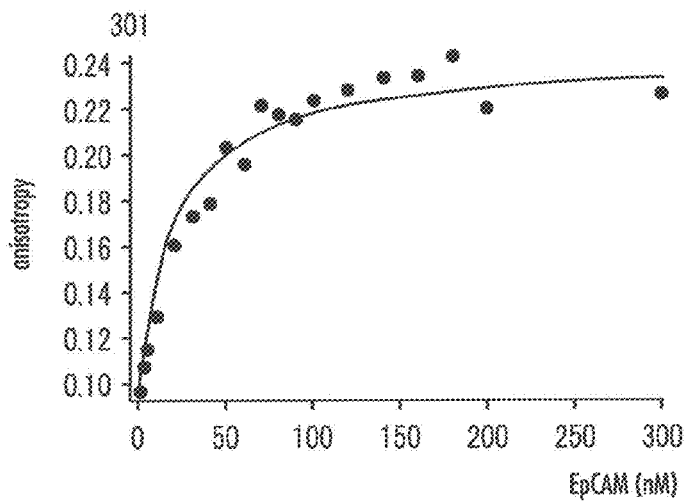
Figure 2E:
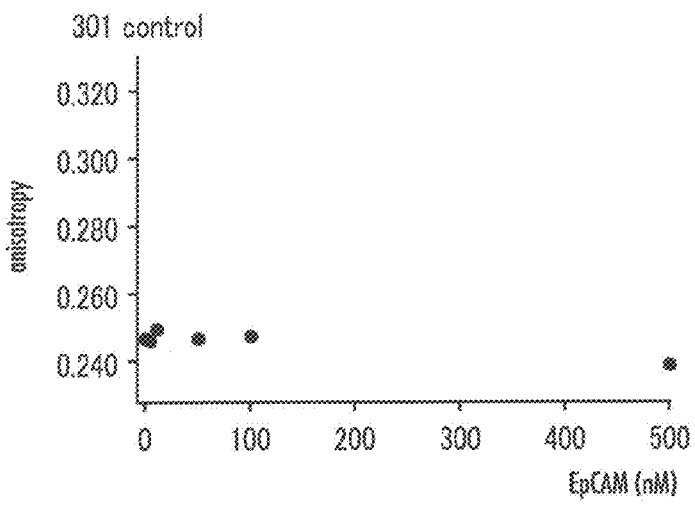
Figure 2F:
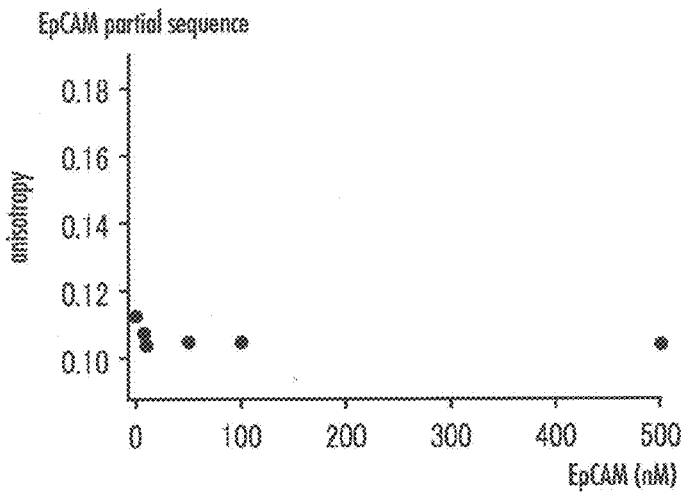

The dissociation constants of the EpCAM-binding peptide Ep301 (FIG. 2(D)) disclosed in Patent Literature 2 and Ep301 control (FIG. 2(E)), which was a control peptide derived from Ep301 by the substitution of cysteine at positions 5 and 10 by serine, and a sequence of EpCAM from residue 106 to 119 (FIG. 2(F)) having partial homology to EpCAM-binding peptides were measured similarly. The results are shown in FIG. 2 and Table 1.

TABLE 1

| Peptide | Sequence | Kd (nM) |
|---|---|---|
| Ep133 | EHLHCLGSLCWP (SEQ ID NO: 2) | 1.5 |
| Ep133 control | EHLHSLGSLSWP (SEQ ID NO: 7) | N.B. |
| Ep114 | KHLQCVRNICWS (SEQ ID NO: 3) | 1.6 |
| Ep301 | KSLQCINNLCWP (SEQ ID NO: 5) | 20.0 |
| Ep301 control | KSLQSINNLSWP (SEQ ID NO: 8) | N.B. |
| EpCAM partial sequence | KAKQCNGTSMCWPK (SEQ ID NO: 9) | N.B. |

N.B.: Not bound.

As described above, the two types of peptides Ep133 and Ep114 newly obtained this time were shown to bind to EpCAM at least 10 times more strongly compared with the previously obtained Ep301.

The peptides in which cysteine at positions 5 and 10 was substituted by serine did not exhibit EpCAM-binding activity, suggesting that the formation of an S—S bond by these two cysteine residues is important for the binding to EpCAM.

The sequence of EpCAM from residues 106 to 119 exhibits partial homology to EpCAM-binding peptides, but was not confirmed to bind to EpCAM.

Example 4

[Analysis of Functional Sites in Ep114 Peptide]

1. Identification of Functional Sites in Ep114 Peptide by Alanine Scanning

In order to identify functional sites in Ep114, phages displaying alanine substitution variants of Ep114 were prepared and analyzed for binding activity against EpCAM and binding activity against an anti-Ep114 antibody.

The anti-EpCAM antibody used was prepared as follows: the synthesized Ep114 peptide was used as an antigen and conjugated with bovine thyroglobin as a carrier protein, followed by the immunization of a rabbit with a total of 8 shots. A rise in antibody titer in the serum was confirmed by a preliminary test, and IgG was purified using IgG affinity chromatography to obtain an anti-Ep114 antibody (IgG).

The alanine substitution variants of Ep114 were prepared by substituting one by one the amino acid residues constituting Ep114 by alanine using a site-directed mutagenesis kit based on inverse PCR, KOD-Plus-Mutagenseis Kit (Toyobo Co., Ltd.). Hereinafter, as for the variants of Ep114, for example, a variant in which lysine (K) at the 1st residue was substituted by alanine (A) is indicated by Ep114(K1A), wherein the amino acid before the variation, the position, and the amino acid after the variation are described within the parenthesis.

The prepared variant phages were analyzed for binding activity against EpCAM and binding activity against the anti-EpCAM antibody by the following methods.

EpCAM or the anti-Ep114 antibody (1 μg/well) was immobilized overnight at 4° C. onto a 96-well plate. The plate was blocked at room temperature for 1 hour with 0.1 M NaHCO$_3$ containing 0.5% BSA and washed with TBST.

Figure 3A:
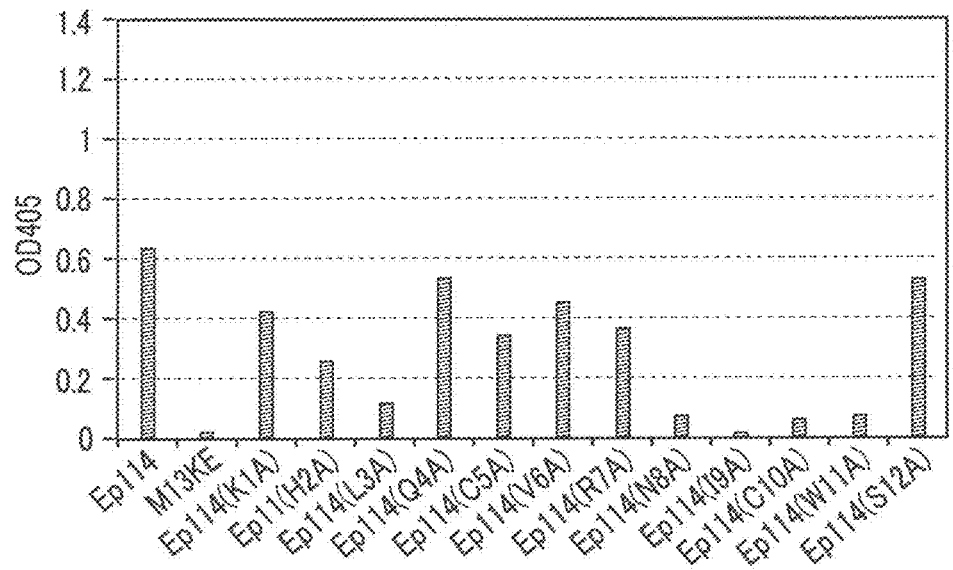
FIG. 3A-3B showing the identification of a functional site in Ep114 using variant phages.
Figure 3B:
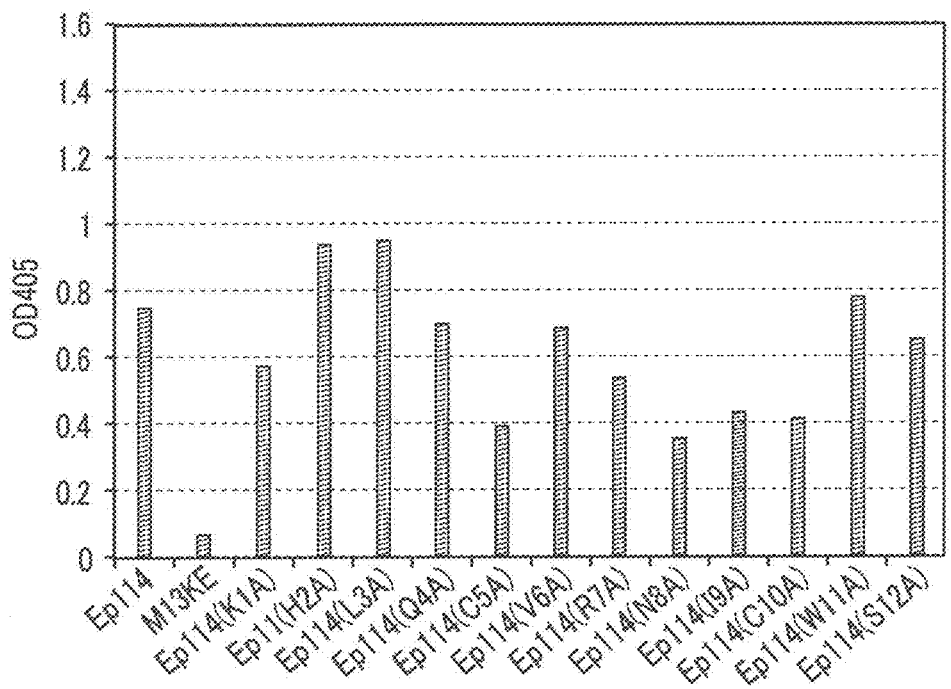

The phages displaying the peptides in which each amino acid of Ep114 was substituted by alanine are added to the EpCAM- or anti-Ep114 antibody-immobilized plate, and the plate is left still at room temperature for 1 hour. After washing with TBST, HRP-labeled anti-M13 antibodies were reacted therewith, followed by detection using ABTS (2,2'-azinobis(3-ethylbenzothiazoline-6-sulfonic acid). The binding activity against EpCAM is shown in FIG. 3A, and the binding activity against the anti-Ep114 antibody is shown in FIG. 3B. M13KE is a phage displaying no peptide and is a negative control.

It was demonstrated that: the binding activity against EpCAM is greatly decreased by the alanine substitution of histidine at the 2nd residue, leucine at the 3rd residue, asparagine at the 8th residue, isoleucine at the 9th residue, cysteine at the 10th residue, or tryptophan at the 11th residue; and the recognition of the anti-Ep114 antibody is decreased by the alanine substitution of cysteine at the 5th residue, asparagine at the 8th residue, isoleucine at the 9th residue, and cysteine at the 10th residue.

Particularly, asparagine at the 8th residue, isoleucine at the 9th residue, and cysteine at the 10th residue influence the binding activity of the peptide both against EpCAM and against the anti-Ep114 antibody, suggesting that these residues are important structurally. The variant Ep114 (L3A) in which lysine at the 3rd residue of Ep114 was substituted by alanine had low binding activity against EpCAM and also exhibited low nonspecific adsorption, and therefore used as a negative control in the subsequent experiments.

2. Effect of Lysine at 1st Residue of Ep114 Peptide on Binding to EpCAM

Lysine at the 1st residue of the Ep114 peptide was substituted by different amino acids, and the binding activity against EpCAM was analyzed. Generally, for modification through binding with a fluorescent molecule or the like after peptide synthesis, a peptide is often synthesized with extra lysine added the C terminus in advance and use of the side chain of this lysine for modification. When lysine is also present at the N terminus, this N-terminal lysine is also modified, making it difficult to adjust the degree of the modification. Accordingly, when lysine at the 1st residue can be substituted by another amino acid, the modification can be achieved by use of only the side chain of the C-terminal lysine. Furthermore, when the N-terminal lysine is unnecessary, a peptide shorter by 1 residue can be synthesized and used for modification so that the cost for peptide synthesis might be saved.

Figure 4A:
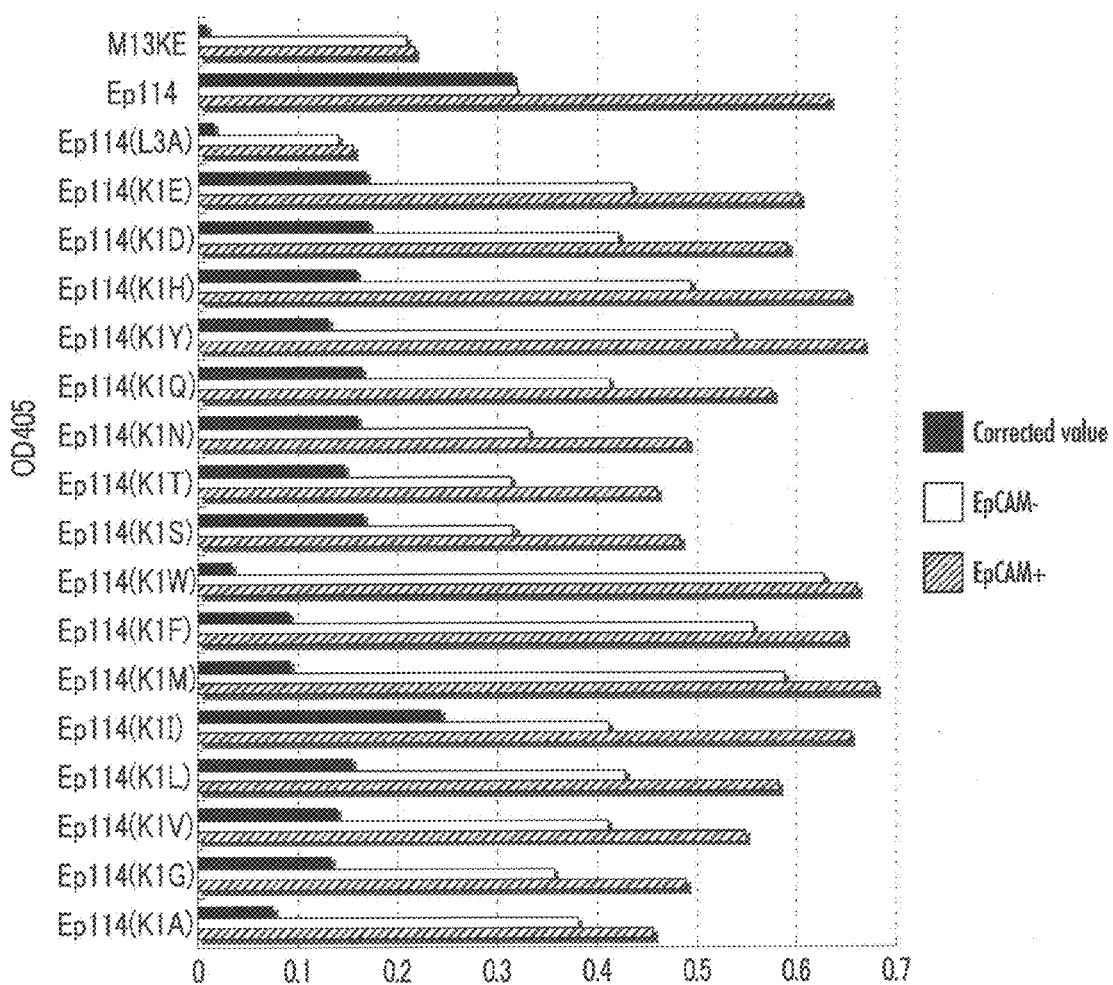
FIGS. 4A and 4B showing the function of lysine at the 1st residue of Ep114 using variant phages.

As with the alanine substitution variants, variant phages were prepared by the introducing specific mutations to lysine at the 1st residue based on inverse PCR method and analyzed for binding activity against EpCAM. The analysis method involved evaluation by ELISA in the same way as in the functional analysis of the Ep114 peptide by the alanine scanning. The results are shown in FIG. 4A. In the figure, EpCAM+ and EpCAM− represent the presence and absence of EpCAM immobilization onto a plate, respectively. Corrected value represents a value subtracting the measurement of EpCAM– from the measurement of EpCAM+. A higher value of EpCAM– indicates that the nonspecific adsorption of the peptide is higher.

The substitution of lysine at the 1st residue of Ep114 by another amino acid did not abolish the ability to bind to EpCAM, though the resulting ability to bind is slightly lower than that of Ep114. However, a tendency to increase nonspecific adsorption was shown, depending on the types of the amino acids. Particularly, the variants in which lysine is substituted by tryptophan (W), phenylalanine (F), methionine (M), or tyrosine (Y) are nonspecifically adsorbed onto a solid phase at an increased rate even when EpCAM is not immobilized on the plate. On the other hand, the variants in which lysine is substituted by asparagine (N), threonine (T), or serine (S) exhibit the similar level of nonspecific adsorption as that of Ep114.

Based on the results of ELISA, the variants in which lysine was substituted by tryptophan (W), phenylalanine (F), methionine (M), or tyrosine (Y) have the reduced ability to bind to EpCAM with increased nonspecific adsorption. Thus, these variants were further analyzed for their ability to bind to EpCAM using beads.

The analysis was conducted using the variants in which lysine at the 1st residue was substituted by alanine (A), asparagine (N), serine (S), or isoleucine (I), and M13KE, Ep114, and the variant in which leucine at the 3rd residue was substituted by alanine as controls. Each phage of 1×10$^{10}$ PFU was bound to 1 μg of EpCAM, and then mixed with 0.4 mg of beads pretreated overnight with 0.5% BSA and B&W buffer (5 mM Tris-HCl (pH 7.5), 0.5 mM EDTA, and 1 M NaCl). The number of phages bound to the beads was counted. The results are shown in FIG. 4B.

Figure 4B:
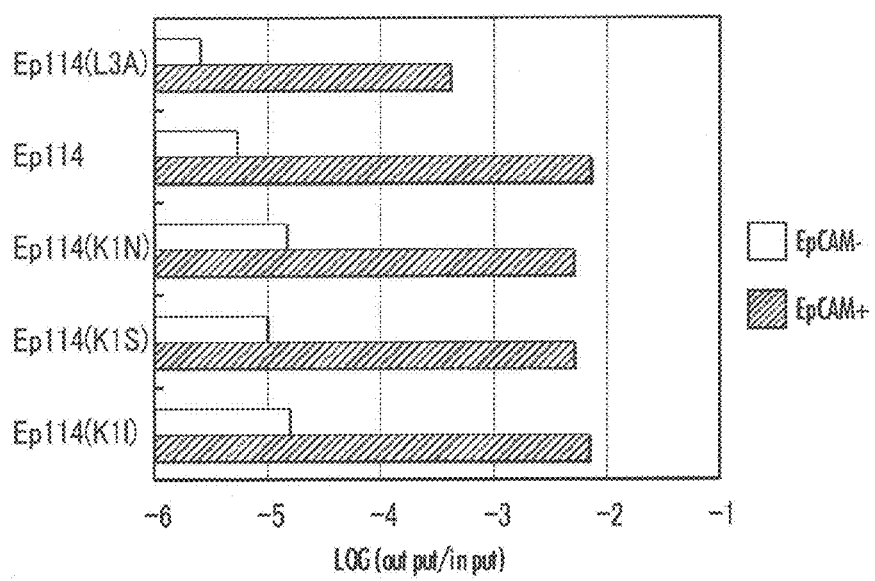

As shown in FIG. 4B, based on results of the experiment using the beads, the variant phages in which lysine at the 1st residue was substituted by the amino acid mentioned above did not largely vary in the ability to bind from Ep114. On the other hand, the L3A variant phage showed the rate of EpCAM binding one digit lower than that of other phages.

Although the result of ELISA and the result of the experiment using beads are seemed different, this is presumably attributed to the difference in the properties of background adsorption between the immobilization using physical adsorption onto a plastic substrate in ELISA and the immobilization using the His tag on magnetic beads. When the background adsorption is offset, it is considered that the ability to bind to EpCAM varies rarely when lysine at the 1st residue is changed to another amino acid.

Example 5

[Application to Immunoprecipitation Method Using Biotinylated Ep114]

The peptide was biotinylated at the stage of its synthesis, immobilized onto streptavidin beads, and analyzed for reactivity with the anti-EpCAM antibody and detection of EpCAM.

1. Binding to Anti-Ep114 Antibody

250 μg of streptavidin-magnetic beads (Dynabeads® M-280 streptavidin, VERITAS Corp.) in TBS containing 2% BSA was added to 20 μg of the biotinylated Ep114 peptide and shaken at room temperature for 30 minutes, followed by washing with TBS. Beads reacted without the peptide were used as a control. The anti-Ep114 antibody was added to the beads in TBST and reacted at room temperature for 1 hour. After washing with TBS, the beads were collected. The collected beads were heated at 95° C. for 5 minutes in a SDS sample buffer. After Western-blotting, the anti-Ep114 antibody was detected using HRP-labeled anti-rabbit antibodies.

A schematic diagram of the reaction with the magnetic beads is shown in the left panel of FIG. 5A, and the Western blot results are shown on the right panel thereof. FIG. 5A shows the results about lane 1: Ep114+the anti-Ep114 antibody, lane 2: Ep114+control serum (Ep114 preimmune serum), lane 3: no peptide+the anti-Ep114 antibody, and lane 4: no peptide+control serum in the bead-bound fraction (Bead:left) and the supernatant (right).

Proteins reactive with the rabbit antibody were detected only in lane 1 in which Ep114 and the anti-Ep114 antibody were added to the magnetic beads for reaction. This indicates that the biotinylated Ep114 peptide was bound with the streptavidin-magnetic beads and further bound with the anti-Ep114 antibody.

2. Binding to EpCAM

The binding of Ep114 to EpCAM was confirmed using the Western blot system in the similar method as in the preceding paragraph 1. Specifically, 20 μg of the biotinylated Ep114 peptide was bound to 250 μg of streptavidin-magnetic beads and then reacted with 400 ng of EpCAM, followed by Western blot to detect EpCAM using anti-EpCAM polyclonal antibodies (see the left panel of FIG. 5B).

In addition to the peptide used in the preceding paragraph 1, 3 types of synthetic peptides (referred to as PE183, PE184, and PE185), which were the linker-added and biotin-modified and represented by sequences (1), (2), and (3) given below, respectively, were examined similarly and confirmed the binding to EpCAM. In the sequences below, the linker moieties are underlined.

```
PE183  Ac-KHLQCVRNICWSPPPPPPKK(biotin)-NH2      (1)
       (SEQ ID NO: 10)

PE184  Ac-KHLQCVRNICWSGGSGGSK(biotin)-NH2       (2)
       (SEQ ID NO: 11)

PE185  Ac-KHLQCVRNICWSNNNNSNNNNK(biotin)-NH2    (3)
       (SEQ ID NO: 12)
```

The results are shown in FIG. 5B. FIG. 5B shows the results about lane 1: no peptide, lane 2: the biotinylated Ep114, lane 3: the PE183 peptide, lane 4: the PE184 peptide, and lane 5: the PE185 peptide in the bead-bound fraction (Bead: left) and the supernatant (right).

The peptides having the amino acid sequence PPPPPPKK or GGSGGSK as the linker shown in lane 3 or 4 bound to EpCAM very highly compared with the linker-free biotinylated peptide or the peptide having the NNNNSNNNNK linker. It is considered that the presence of a appropriate linker sequence allows Ep114 to bind to EpCAM without steric inhibition.

3. Binding to Exosome

The binding to exosomes was confirmed using the Western blot system in the similar method as in the preceding paragraph 1. Specifically, 20 μg of the biotinylated Ep114 peptide, the PE183 peptide, the PE184 peptide, or the PE185 peptide was bound to 250 μg of streptavidin-magnetic beads and then reacted with exosomes isolated from HT-29 cells as EpCAM-positive cells, followed by Western blot to detect the exosomes using anti-EpCAM polyclonal antibodies (see the left panel of FIG. 5C).

The peptides with any of the linkers and the linker-free biotinylated peptide showed the equivalent ability to bind to the exosomes.

Example 6

[Detection Using Fluorescent Labeling]

The binding of each peptide of the present invention to EpCAM was detected using fluorescent labeling. Exosomes fluorescently labeled with PKH26 (Sigma-Aldrich Corp.) were used to detect the binding of the peptide (FIG. 6).

20 μg of the biotinylated Ep114 peptide (1), the PE183 peptide (2), the PE184 peptide (3), or the PE185 peptide (4) was bound to 250 μg of streptavidin-magnetic beads, followed by washing, and the fluorescent intensity was measured. Then, the PKH26-labeled exosomes were added thereto and reacted at room temperature for 1 hour, followed by washing. The fluorescence intensity of each sample was measured. FIG. 6 shows increase in fluorescence intensity relative to the control.

When any of the biotinylated peptides was used, enhanced fluorescence intensity compared with the control was detected, indicating that exosomes may be fluorescently labeled and used in the assay.

Example 7

[Detection by ELISA]
The PE183 peptide

Figure 7A:
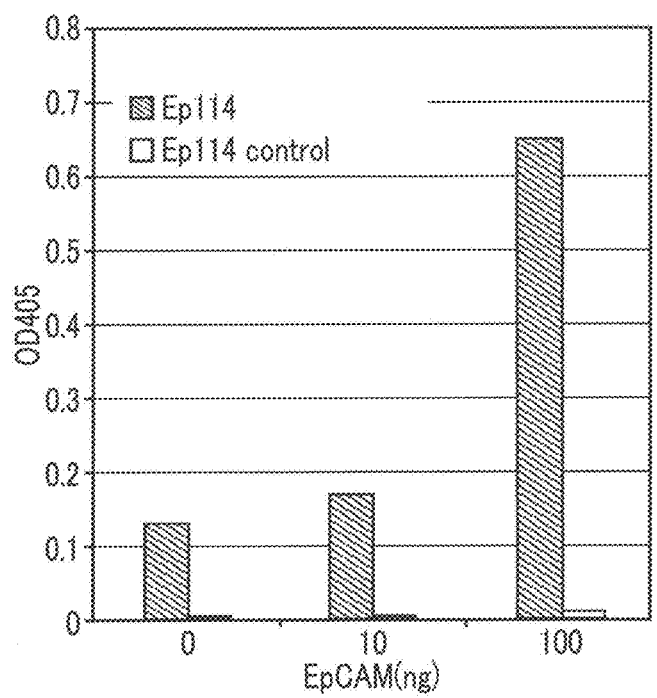
FIGS. 7A and 7B showing an example of detection by ELISA using Ep114.

```
         (Ac-KHLQCVRNICWSPPPPPPKK(biotin)-NH2,
SEQ ID NO: 10)
``` was immobilized onto an ELISA plate via streptavidin, and purified EpCAM was added thereto in an amount of 0, 10, or 100 ng and reacted. After washing, bound EpCAM was detected using the anti-EpCAM antibody. A biotin-modified peptide PE194 (Ac-KHAQCVRNICWSPPPPPPKK(biotin)-NH2) (SEQ ID NO: 13) of the L3A variant (non-EpCAM-binding variant) was used as a control. The results are shown in FIG. 7A.

In the case of using the PE183 peptide, enhancement in ELISA signal proportional to the amount of EpCAM added was observed. On the other hand, increase in signal intensity was rarely observed in the non-EpCAM-binding variant after the amount of EpCAM added was increased.

Next, the PE183 peptide

Figure 7B:
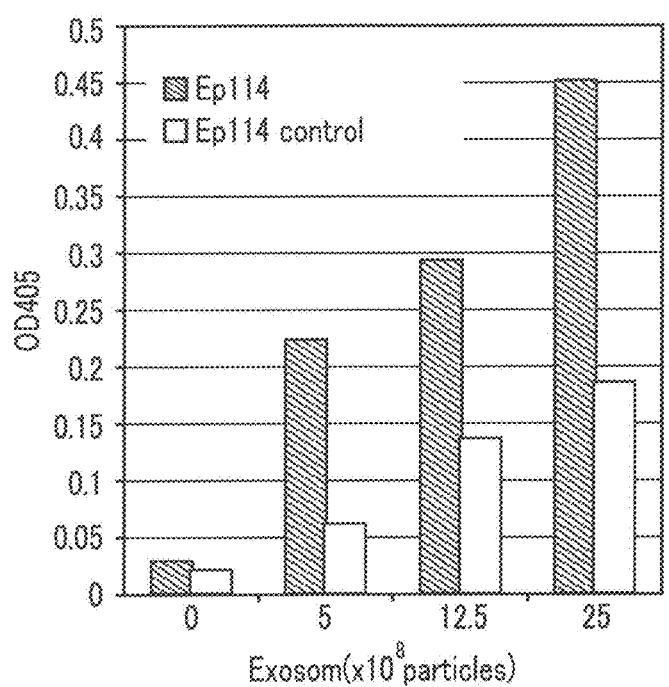

```
         (Ac-KHLQCVRNICWSPPPPPPKK(biotin)-NH2,
SEQ ID NO: 10)
``` was immobilized onto an ELISA plate via streptavidin, and HT-29-derived exosomes were added thereto and reacted. After washing, bound exosomes were detected using the anti-EpCAM antibody. The biotin-modified peptide PE194 of the L3A variant was immobilized in the same way as above and used as a control. The results are shown in FIG. 7B.

With increase in the added exosomes, enhancement in ELISA signal was observed in the Ep114 peptide-immobilized sample.

Example 8

[Detection Using Ferritin-Fused Ep114 Peptide]

Because ferritin contains a high electron density of iron hydroxide, it has been used as a label in electron microscopy. In recent years, ferritin has reported to serve as a useful label for image analysis in MRI and thus has received attention. Ep114 was fused to the N terminus of Fer8 (Non Patent Literature 6), a ferritin derivative, and used in analysis.

Figure 8A:
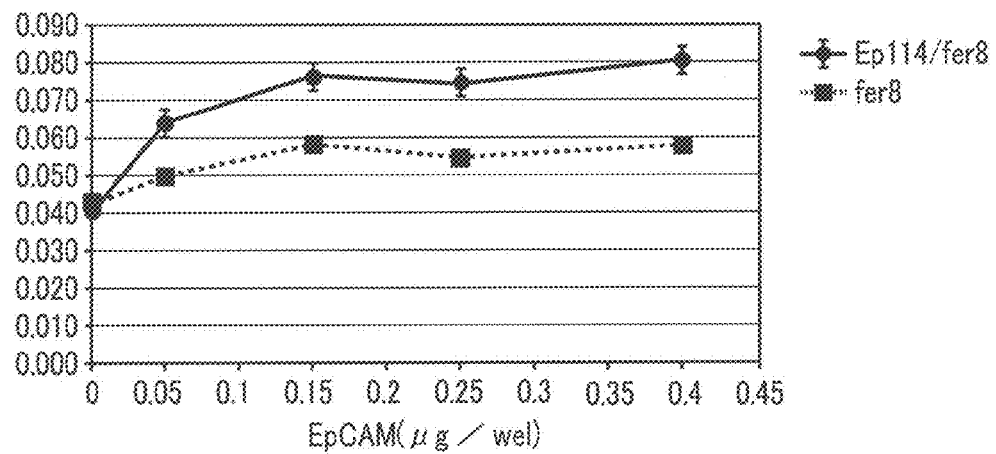
FIGS. 8A and 8B showing an example of application using ferritin-Ep114.

1 μg of the ferritin-fused Ep114 peptide (Ep114/fer8) or ferritin (fer8) was immobilized onto an ELISA plate. Then, purified EpCAM was added thereto at different concentrations. Bound EpCAM was detected using the anti-EpCAM antibody (FIG. 8A).

Figure 8B:
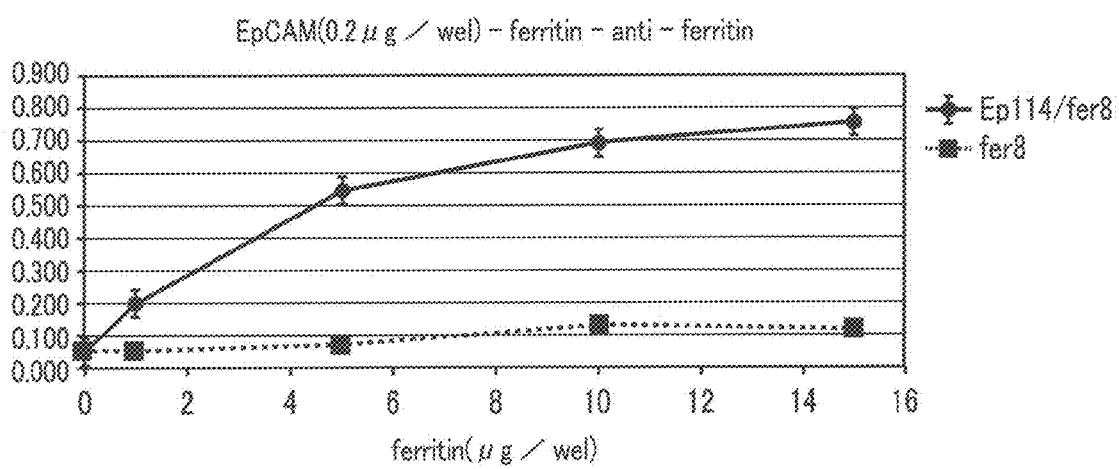

Next, 0.2 μg of purified EpCAM was immobilized onto an ELISA plate. Then, the ferritin-fused Ep114 peptide (Ep114/fer8) or ferritin (fer8) was added thereto at different concentrations. Bound Ep114 peptide (Ep114/fer8) or ferritin (fer8) was detected using an anti-ferritin antibody (FIG. 8B).

The ferritin-fused Ep114 peptide is also capable of sensitively detecting EpCAM. Its application to treatment or diagnosis with MRI can therefore be expected.

Example 9

[Application to Staining Cell]

The Ep301 peptide previously disclosed by the present inventors was confirmed to bind to EpCAM only in a state displayed on a phage and was not confirmed to bind thereto in itself. Thus, the Ep301 peptide separated from the phage was unavailable in staining cell. As shown above in Table 1, the two types of peptides obtained this time bind to EpCAM with strength at least 10 times higher than that of the Ep301 peptide. Thus, it was considered that these peptides might be adequately useful in cell staining in a condition that they were separated from the phages. Accordingly, the staining of spheroid-cultured cell clusters was carried out.

The HT-29 cells as EpCAM-expressing cells were cultured by spheroid culture method as follows: $4 \times 10^5$ cells are suspended in 3 ml of D-MEM/F-12 medium (Dulbecco's Modified n Eagle Medium:Nutrient Mixture 12, 1:1 mixture) (Gibco/Life Technologies Inc.) supplemented with 20 ng/ml human EGF (Miltenyi Biotec K.K.), 20 ng/ml human EGF-2 (Miltenyi Biotec K.K.), B-27 (Gibco/Life Technologies Inc.), penicillin, and streptomycin and inoculated to EZ-Sphere®, a Petri dish of 3.5 cm in diameter coated with MPC polymer. After static culture for 72 hours, the cells were collected while the medium was suspended by pipetting. The cells were stained with the FITC-modified peptide and observed under a fluorescence microscope. The staining was carried out by adding 4 μM peptide into a McCoy's 5A medium and standing still at room temperature for 30 minutes.

Figure 9A:
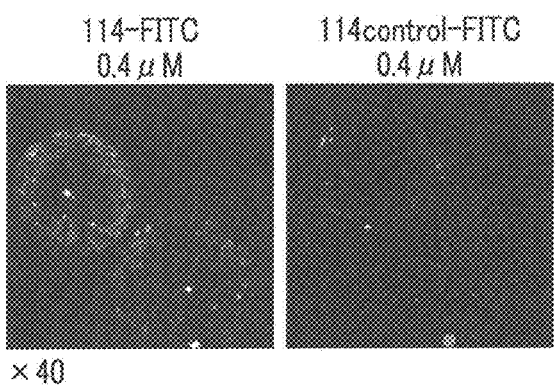
FIG. 9A-9C showing the staining of spheroid-cultured cells with an EpCAM peptide.
Figure 9B:
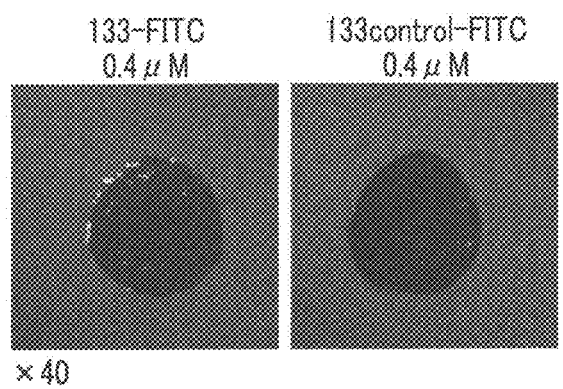
Figure 9C:
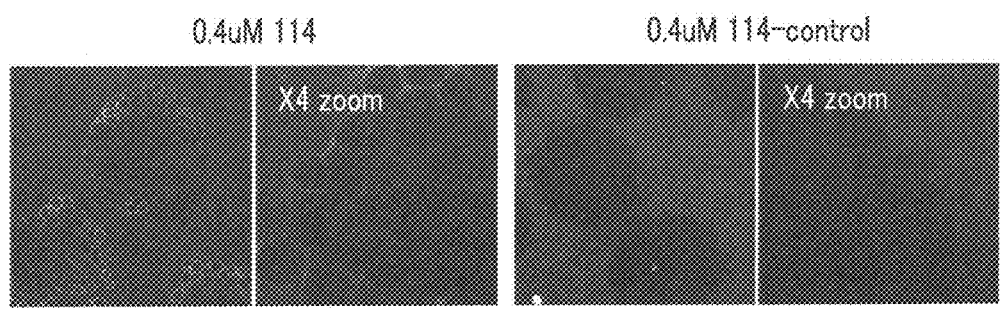

The staining results are shown in FIG. 9. When any of the FITC-labeled Ep114 peptide (FIG. 9A; 114-FITC) and Ep133 peptide (FIG. 9B; 133-FITC) was used, EpCAM on HT-29 was stained at a concentration of 0.4 μM. By contrast, in the case of using control peptides in which cysteine at positions 5 and 10 is substituted by serine, no staining is observed (FIG. 9A; 114control-FITC, FIG. 9B; 133control-FITC). When these control peptides were used at a concentration of 4 μM, no EpCAM staining was observed (data not shown).

In addition to HT-29 cells, the staining of EpCAM using Ep114 was also confirmed by a similar method in MCF-7 cells known to express EpCAM (data not shown).

Next, the results of staining using the L3A variant peptide as a control are shown. The obtained results of staining the spheroids of HT-29 cells demonstrated that the cells were stained with the Ep114 peptide, but not with the L3A variant, as in FIG. 9A.

Example 10

[Application to Cell Staining]

The EpCAM-expressing cells HT-29 or the non-expressing cells Hs578T were cultured in a medium containing 10% fetal calf serum in a Petri dish for 48 hours and then incubated at 37° C. for 1 hour with the FITC-labeled Ep114 peptide or a L3A control labeled peptide at a final concentration of 0.4 µM Immediately thereafter, the cells were observed under a confocal microscope.

The results are shown in FIG. 10. The staining of the cell membrane portions of the EpCAM-expressing cells HT-29 was observed with the Ep114 peptide, whereas no staining was observed with the control peptide or the non-EpCAM-expressing cells Hs578T cells.

Example 11

[Cross-Linking of Cysteine in Ep114]

Cysteines at the 5th and 10th amino acid are conserved in all of the Ep133 peptide and the Ep114 peptide, and the previously disclosed Ep301 peptide, suggesting the importance of cysteine. As shown in Example 3, the substitution of these two cysteine residues by serine abolishes the binding activity against EpCAM, also suggesting the importance of the cysteine residues.

The present inventors have further found that the Ep301 peptide forms an S—S bond by oxidation treatment and thereby gain binding activity against EpCAM. As for Ep133 cloned this time, after formation of an S—S bond between the cysteine residues by oxidation treatment and fractionation by HPLC, only a fraction of the peptides having the S—S bond showed binding activity against EpCAM.

By contrast, the Ep114 peptide showed no binding activity against EpCAM when the ability to bind is measured by the fluorescence depolarization method immediately after chemical synthesis. The peptide, however, was rapidly oxidized in the presence of 10% FCS so that its binding to EpCAM is observed even without active oxidation treatment.

Figure 11:
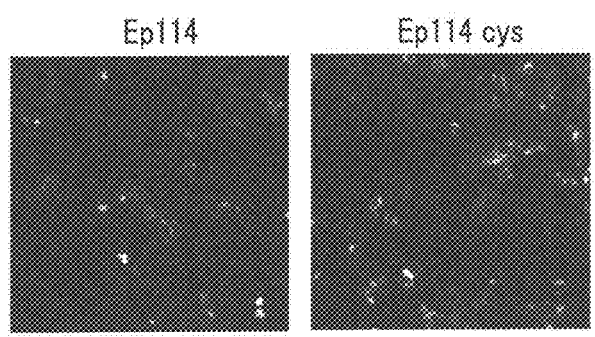
FIG. 11 showing that Ep114 forms an S—S bond by autoxidation.

FIG. 11 shows staining cells using the FITC-modified Ep114 peptide. 293T cells expressing no endogenous EpCAM were transfected with pkk196, an expression plasmid in which the full-length EpCAM gene incorporated, and forced to express EpCAM, followed by staining using FITC-modified Ep114. The peptide in which an S—S bond was actively formed by oxidation treatment (left of FIG. 11, Ep114) and the peptide that did not undergo no oxidation treatment (right of FIG. 11, Ep114Cys) both had the equivalent ability to stain EpCAM. By contrast, the Ep133 peptide did not show the ability to bind to EpCAM unless active oxidation treatment was performed (data not shown).

The S—S bond formation of Ep114 was studied in detail using the fluorescence depolarization method and HPLC. As a result, it was demonstrated that this peptide in PBS at 4° C. or frozen at −20° C. is oxidized after 10 days to form an S—S bond (data not shown).

This property of Ep114 of forming an S—S bond even without oxidation treatment and thereby exhibiting the ability to bind to EpCAM means that the chemically synthesized peptide can be used as it is. Such a peptide is very useful for use in clinical application or the like.

As described above, the two types of EpCAM-binding peptides Ep133 and Ep114 disclosed in the present invention have the strong ability to bind to EpCAM, and as such, are very useful in the diagnosis and prognosis of cancer.

As demonstrated above, the present invention provides a peptide that exhibits the high ability to bind to EpCAM, and shows application methods using the peptide.

Because of the strong ability to bind to EpCAM, the peptide of the present invention can be used as a carrier for a drug delivery system targeting cells expressing EpCAM on the surface of cells and can also be expected to be applied as an active substance for use in, for example, treatment through binding to a toxin such as diphtheria toxin, though these are not shown herein.

Moreover, the peptide can be chemically synthesized and can therefore provide a large amount of a product with an inexpensive cost, stable quality and the reduced risk of being contaminated with impurities during the process of purification.

Furthermore, since the antibody against the peptide of the present invention has already been obtained, a wide range of application based on immunological approaches commonly used can be achieved by use of the anti-peptide antibody.

The invention claimed is:

1. A peptide that has the ability to bind to EpCAM wherein the peptide consisting of the amino acid sequence shown in SEQ ID NO: 2 (EHLHCLGSLCWP; Ep133).

2. A peptide that has the ability to bind to EpCAM wherein the peptide consisting of the amino acid sequence shown in SEQ ID NO: 3 (KHLQCVRNICWS; Ep114).

3. The peptide according to claim 1, wherein the peptide is labeled with a detectable marker.

4. A fusion peptide in which the peptide according to claim 1 is covalently bound with a marker protein and/or a peptide tag.

5. An EpCAM-peptide complex in which the peptide according to claim 1 is bound with EpCAM.

6. A phage that has the ability to bind to EpCAM, wherein the phage displays the peptide according to claim 1 on the particle surface thereof.

7. A composition comprising the peptide according to claim 1.

8. A method for detecting and/or quantifying EpCAM, comprising using the peptide according to claim 1.

9. The peptide according to claim 2, wherein the peptide is labeled with a detectable marker.

10. A fusion peptide in which the peptide according to claim 2 is covalently bound with a marker protein and/or a peptide tag.

11. An EpCAM-peptide complex in which the peptide according to claim 2 is bound with EpCAM.

12. A phage that has the ability to bind to EpCAM, wherein the phage displays the peptide according to claim 2 on the particle surface thereof.

13. A method for detecting and/or quantifying EpCAM, comprising using the peptide according to claim 2.

* * * * *

SEQUENCE LISTING

```
<160> NUMBER OF SEQ ID NOS: 13

<210> SEQ ID NO 1
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (12)..(12)
```

<223> OTHER INFORMATION: Xaa can be any naturally occurring amino acid

<400> SEQUENCE: 1

Xaa His Leu Xaa Cys Xaa Xaa Xaa Xaa Cys Trp Xaa
1               5                   10

<210> SEQ ID NO 2
<211> LENGTH: 12
<212> TYPE: PRT
<213> ORGANISM: Artificial Sequence
<220> FEATURE:
<223> OTHER INFORMATION: synthetic

<400> SEQUENCE: 2

Glu His Leu His Cys Leu Gly Ser Leu Cys Trp Pro
1               5                   10

<210> SEQ ID NO 3
<211> LENGTH: 12
<212> TYPE: PRT
<213> ORGANISM: Artificial Sequence
<220> FEATURE:
<223> OTHER INFORMATION: synthetic

<400> SEQUENCE: 3

Lys His Leu Gln Cys Val Arg Asn Ile Cys Trp Ser
1               5                   10

<210> SEQ ID NO 4
<211> LENGTH: 20
<212> TYPE: DNA
<213> ORGANISM: Artificial Sequence
<220> FEATURE:
<223> OTHER INFORMATION: synthetic

<400> SEQUENCE: 4
ccctcatagt tagcgtaacg                                               20

<210> SEQ ID NO 5
<211> LENGTH: 12
<212> TYPE: PRT
<213> ORGANISM: Artificial Sequence
<220> FEATURE:
<223> OTHER INFORMATION: synthetic

<400> SEQUENCE: 5

Lys Ser Leu Gln Cys Ile Asn Asn Leu Cys Trp Pro
1               5                   10

<210> SEQ ID NO 6
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: K or R
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: L, I, M, or V
<220> FEATURE:
<221> NAME/KEY: misc_feature

```
<222> LOCATION: (6)..(6)
<223> OTHER INFORMATION: L, I, M, or V
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: N, Q, H or K
<220> FEATURE:
<221> NAME/KEY: misc_feature
<222> LOCATION: (9)..(9)
<223> OTHER INFORMATION: L, I, M, or V
<220> FEATURE:
<221> NAME/KEY: misc_feature
<222> LOCATION: (12)..(12)
<223> OTHER INFORMATION: Xaa can be any naturally occurring amino acid

<400> SEQUENCE: 6

Xaa Xaa Xaa Gln Cys Xaa Xaa Xaa Xaa Cys Trp Xaa
1               5                   10

<210> SEQ ID NO 7
<211> LENGTH: 12
<212> TYPE: PRT
<213> ORGANISM: Artificial Sequence
<220> FEATURE:
<223> OTHER INFORMATION: synthetic

<400> SEQUENCE: 7

Glu His Leu His Ser Leu Gly Ser Leu Ser Trp Pro
1               5                   10

<210> SEQ ID NO 8
<211> LENGTH: 12
<212> TYPE: PRT
<213> ORGANISM: Artificial Sequence
<220> FEATURE:
<223> OTHER INFORMATION: synthetic

<400> SEQUENCE: 8

Lys Ser Leu Gln Ser Ile Asn Asn Leu Ser Trp Pro
1               5                   10

<210> SEQ ID NO 9
<211> LENGTH: 14
<212> TYPE: PRT
<213> ORGANISM: Homo sapiens

<400> SEQUENCE: 9

Lys Ala Lys Gln Cys Asn Gly Thr Ser Met Cys Trp Pro Lys
1               5                   10

<210> SEQ ID NO 10
<211> LENGTH: 20
<212> TYPE: PRT
<213> ORGANISM: Artificial Sequence
<220> FEATURE:
<223> OTHER INFORMATION: synthetic

<400> SEQUENCE: 10

Lys His Leu Gln Cys Val Arg Asn Ile Cys Trp Ser Pro Pro Pro
1               5                   10                  15

Pro Pro Lys Lys
            20

<210> SEQ ID NO 11
```

```
<211> LENGTH: 19
<212> TYPE: PRT
<213> ORGANISM: Artificial Sequence
<220> FEATURE:
<223> OTHER INFORMATION: synthetic

<400> SEQUENCE: 11

Lys His Leu Gln Cys Val Arg Asn Ile Cys Trp Ser Gly Gly Ser Gly
1               5                   10                  15

Gly Ser Lys

<210> SEQ ID NO 12
<211> LENGTH: 22
<212> TYPE: PRT
<213> ORGANISM: Artificial Sequence
<220> FEATURE:
<223> OTHER INFORMATION: synthetic

<400> SEQUENCE: 12

Lys His Leu Gln Cys Val Arg Asn Ile Cys Trp Ser Asn Asn Asn Asn
1               5                   10                  15

Ser Asn Asn Asn Asn Lys
            20

<210> SEQ ID NO 13
<211> LENGTH: 20
<212> TYPE: PRT
<213> ORGANISM: Artificial Sequence
<220> FEATURE:
<223> OTHER INFORMATION: synthetic

<400> SEQUENCE: 13

Lys His Ala Gln Cys Val Arg Asn Ile Cys Trp Ser Pro Pro Pro Pro
1               5                   10                  15

Pro Pro Lys Lys
            20
```